United States Patent [19]

Ri et al.

[11] Patent Number: 5,615,679
[45] Date of Patent: Apr. 1, 1997

[54] METHOD OF DISPLAYING ULTRASONIC IMAGES AND APPARATUS FOR ULTRASONIC DIAGNOSIS

[75] Inventors: Taiho Ri; Shinichi Amemiya; Takao Jibiki, all of Tokyo, Japan

[73] Assignee: GE Yokogawa Medical Systems, Limited, Tokyo, Japan

[21] Appl. No.: 573,621

[22] Filed: Dec. 18, 1995

[30] Foreign Application Priority Data

Feb. 6, 1995 [JP] Japan ..................................... 7-018131

[51] Int. Cl.⁶ ..................................................... A61B 8/00
[52] U.S. Cl. ...................................................... 128/660.05
[58] Field of Search ......................... 128/661.04, 661.08, 128/661.09, 661.1, 662.01, 662.02, 691, 660.07, 660.05

[56] References Cited

U.S. PATENT DOCUMENTS 5,148,809  9/1992  Biegeleisen-Knight et al. .. 128/660.07
5,285,788  2/1994  Arenson et al. .................... 128/662.02
5,446,800  8/1995  Briggs et al. ...................... 128/661.08

*Primary Examiner*—George Manuel
*Attorney, Agent, or Firm*—Moonray Kojima

[57] ABSTRACT

In an apparatus for ultrasonic diagnosis, an autocorrelation calculator 11 produces Doppler power data P, a shading portion extractor 21 extracts the left-side section of the profile of the ultrasonic image from the Doppler power data P, and a data value converter 22 converts the data value of the extracted shading portion into the data value for shading and converts the data values of remaining portions into a data value different from the data value for shading. The shaded ultrasonic image is visualized as a three-dimensional image so as to facilitate the diagnosis. Particularly, in ultrasonic images of Doppler power mode, blood vessels are visualized as three-dimensional images, and the viewer can identify even small blood vessels accurately.

18 Claims, 7 Drawing Sheets

Data Value Conversion

METHOD OF DISPLAYING ULTRASONIC IMAGES AND APPARATUS FOR ULTRASONIC DIAGNOSIS

BACKGROUND OF THE INVENTION

The present invention relates to a method of displaying ultrasonic images and apparatus for ultrasonic diagnosis, and particularly to a method of displaying ultrasonic images and apparatus for ultrasonic diagnosis with the enhanced ability of depicting small blood vessels in Doppler power mode.

FIG. 9 is a block diagram showing a conventional apparatus for ultrasonic diagnosis. The ultrasonic diagnostic apparatus 500 includes a ultrasonic probe 1 and ultrasonic wave transmitter/receiver 2, by which multiple ultrasonic pulses are transmitted at a certain time interval and ultrasonic echo signals from multiple observation points in depth direction on multiple ultrasonic beam lines are received.

In Doppler power mode, the ultrasonic echo signals are fed to an orthogonal detector 4. The orthogonal detector 4 includes mixers 4a and 4b, by which the ultrasonic echo signals are multiplied to reference signals provided by reference signal generators 4c and 4d, and it produces an orthogonal component Q and in-phase component I at the outputs of low-pass filters (LPFs) 4h and 4i. A/D converters 5 and 6 render the A/D conversion for the orthogonal component Q and in-phase component I, and store the resulting data in memories 7 and 8.

Moving target indication (MTI) filters 9 and 10 read the orthogonal component Q and in-phase component I out of the memories 7 and 8, and remove unneedful clutter components (Doppler components from such tissues as the wall of heat having a relatively slow movement) from these components Q and I. An autocorrelation calculator 11 calculates power data $P(R,\phi)$ (where R represents the depth of observation point and $\phi$ represents the beam line number) from the orthogonal component Q and in-phase component I that have been rid of the unneedful components.

A digital scan converter (DSC) 13 converts the power data $P(R,\phi)$ into pixel values and implements the two-dimensional mapping for the pixel values based on the positions of observation points, thereby yielding image data DI. A CRT display unit 14 displays a ultrasonic image of Doppler power mode derived from the image data DI.

FIG. 10 shows an example of ultrasonic images of Doppler power mode. Displayed in this example over the background H, which is generally black, are blood vessels P1 and P2 in the orange color and at various luminance levels depending on the magnitude of the power.

Returning to FIG. 9, in color flow mapping (CFM) mode, the autocorrelation calculator 11 implements the calculation of autocorrelation between ultrasonic pulses for the orthogonal component Q and in-phase component I, thereby producing velocity data $v(R,\phi)$. The DSC 13 converts the velocity data $v(R,\phi)$ into pixel values, implements the two-dimensional mapping for the pixel values based on the positions of observation points, thereby yielding image data DI.

The CRT display unit 14 displays a ultrasonic image of CFM mode derived from the image data DI. For ultrasonic images of CFM mode, the background is generally black, and blood vessels are displayed in red and blue and at various luminance levels depending on the blood flow velocity and direction.

In B mode, the ultrasonic echo signals are fed to a B-mode processor 3. The B-mode processor 3 produces B-mode data from the magnitude of ultrasonic echo signals and delivers the resulting data to the DSC 13. The DSC 13 converts the B-mode data into pixel values and implements the two-dimensional mapping for the pixel values based on the positions of observation points, thereby yielding image data DI.

The CRT display unit 14 displays a ultrasonic image of B mode derived from the image data DI. For ultrasonic images of B mode, the background is generally black, and tissues are displayed in achromatic colors of various luminance levels depending on the magnitude of the ultrasonic echo signals.

However, the conventional ultrasonic diagnostic apparatus 500, which produces ultrasonic images of Doppler power mode as shown in FIG. 10, is not capable of showing clearly the border between the blood vessel images P1 and P2 and the background H, and therefore it is difficult for the viewer to identify small blood vessels accurately.

SUMMARY OF THE INVENTION

An object of the present invention is to provide a method of displaying ultrasonic images and apparatus for ultrasonic diagnosis with the enhanced ability of depicting small blood vessels in Doppler power mode.

In a first aspect of this invention, a ultrasonic image display method transmits ultrasonic waves into a body under test, receives ultrasonic echo signals from the inside of the body, and displays a ultrasonic image produced from the ultrasonic echo signals, wherein the method shades part of the profile section of the image.

In a second aspect of this invention, which is derived from the ultrasonic image display method mentioned above, the range of pixel values of image portions that are not shaded does not include the pixel value of the shaded portion.

In a third aspect of this invention, which is derived from the ultrasonic image display method mentioned above, ultrasonic images are shaded, the shaded images are rendered the time-wise averaging and the averaged image is displayed, or ultrasonic images which are not shaded are rendered the time-wise averaging, the averaged image is shaded and the shaded image is displayed.

In a fourth aspect of this invention, an apparatus for ultrasonic diagnosis comprises data acquisition means which transmits ultrasonic waves and receives ultrasonic echo signals thereby to obtain data of observation points, image forming means which forms a ultrasonic image based on the data, and image display means which displays the image, wherein the image forming means shades the profile section of the image.

In a fifth aspect of this invention, an apparatus for ultrasonic diagnosis comprises data acquisition means which transmits ultrasonic waves along multiple ultrasonic beam lines in different directions and receives ultrasonic echo signals thereby to obtain data of multiple observation points on the beam lines, image forming means which forms a ultrasonic image based on the data, and image display means which displays the image, wherein the apparatus further includes shading portion extraction means which extracts an image portion to be shaded out of the data, and data value conversion means which converts the data value of the shading portion into the data value for shading and converts the data values of remaining portions into a data value different from the data value for shading.

In a sixth aspect of this invention, which is derived from the ultrasonic diagnostic apparatus mentioned above, the shading portion extraction means and data value conversion means comprise a buffer memory which holds beam line data and a lookup table which is addressed by the beam line data held in the buffer memory.

In a seventh aspect of this invention, which is derived from the ultrasonic diagnostic apparatus mentioned above, the apparatus further include data time-averaging means which implements the time-wise averaging for the data released by the data value conversion means and delivers the averaged data to the image forming means.

In a eighth aspect of this invention, which is derived from the ultrasonic diagnostic apparatus mentioned above, the data is data of Doppler power mode.

The ultrasonic image display method of the first aspect is designed to display a ultrasonic image by shading part of the profile section of the image. Consequently, the viewer can visualize three-dimensional ultrasonic images of blood vessels in Doppler power mode and can identify small blood vessels accurately.

The ultrasonic image display method of the second aspect is designed such that in shading part of the profile section of a ultrasonic image, the range of pixel values of image portions that are not shaded does not include the pixel value of a shaded portion. Consequently, ultrasonic images of Doppler power mode enable the viewer to distinguish clearly blood vessels from their shadows and background.

The ultrasonic image display method of the third aspect is designed to shade part of the profile section of multiple ultrasonic images, implement the time-wise averaging process for the shaded images and display the averaged image, or implement the time-wise averaging for multiple ultrasonic images that are not shaded, shade part of the profile section of the averaged image and display the shaded image. Consequently, noises which emerge at random are virtually eliminated from the displayed image. Moreover, in displaying ultrasonic images of Doppler power mode on a real-time basis, the continuous variation of the power of blood vessels is visualized as after images, and the viewer can identify blood vessels more accurately.

The ultrasonic diagnostic apparatus of the fourth aspect is designed to display a ultrasonic image by shading part of the profile section of the image. Consequently, the viewer can visualize three-dimensional ultrasonic images of blood vessels in Doppler power mode and can identify small blood vessels accurately.

The ultrasonic diagnostic apparatus of the fifth aspect is designed such that the data acquisition means obtains data of multiple observation points on multiple ultrasonic beam lines, the shading portion extraction means extracts an image portion to be shaded out of the data, the data value conversion means converts the data value of the extracted image portion into the data value for shading and converts data values of remaining portions into a value different from the data value for shading, the image forming means forms a ultrasonic image based on the converted data, and the image display means displays the resulting image. Consequently, the viewer can visualize three-dimensional images of blood vessels in Doppler power mode, to thereby identify small blood vessels accurately. The viewer can also distinguish clearly blood vessels from their shadows and background.

The ultrasonic diagnostic apparatus of the sixth aspect is designed to have its shading portion extraction means and data value conversion means formed of a buffer memory which holds beam line data and a lookup table which is addressed by the beam line data held in the buffer memory. Consequently, it becomes possible to extract image portions to be shaded and convert data values in a short processing time, and display ultrasonic images on a real-time basis.

The ultrasonic diagnostic apparatus of the seventh aspect is designed to include the data time-averaging means which implements the time-wise averaging for the data released by the data value conversion means and delivers the averaged data to the image forming means, or implements the time-wise averaging for the data provided by the data acquisition means and delivers the averaged data to the shading portion extraction means and data value conversion means. Consequently, noises which emerge at random are virtually eliminated from the displayed image. Moreover, in displaying ultrasonic images of Doppler power mode on a real-time basis, the continuous variation of the power of blood vessels is visualized as after images, and the viewer can identify blood vessels more accurately.

The ultrasonic diagnostic apparatus of the eighth aspect is designed to implement the extraction of an image portion to be shaded and the conversion of data values for data of Doppler power mode. Consequently, the apparatus has the enhanced ability of depicting small blood vessels in Doppler power mode.

DESCRIPTION OF THE PREFERRED EMBODIMENTS

The embodiments of the present invention will be explained in detail with reference to the drawings.

Embodiment 1

Figure 1:
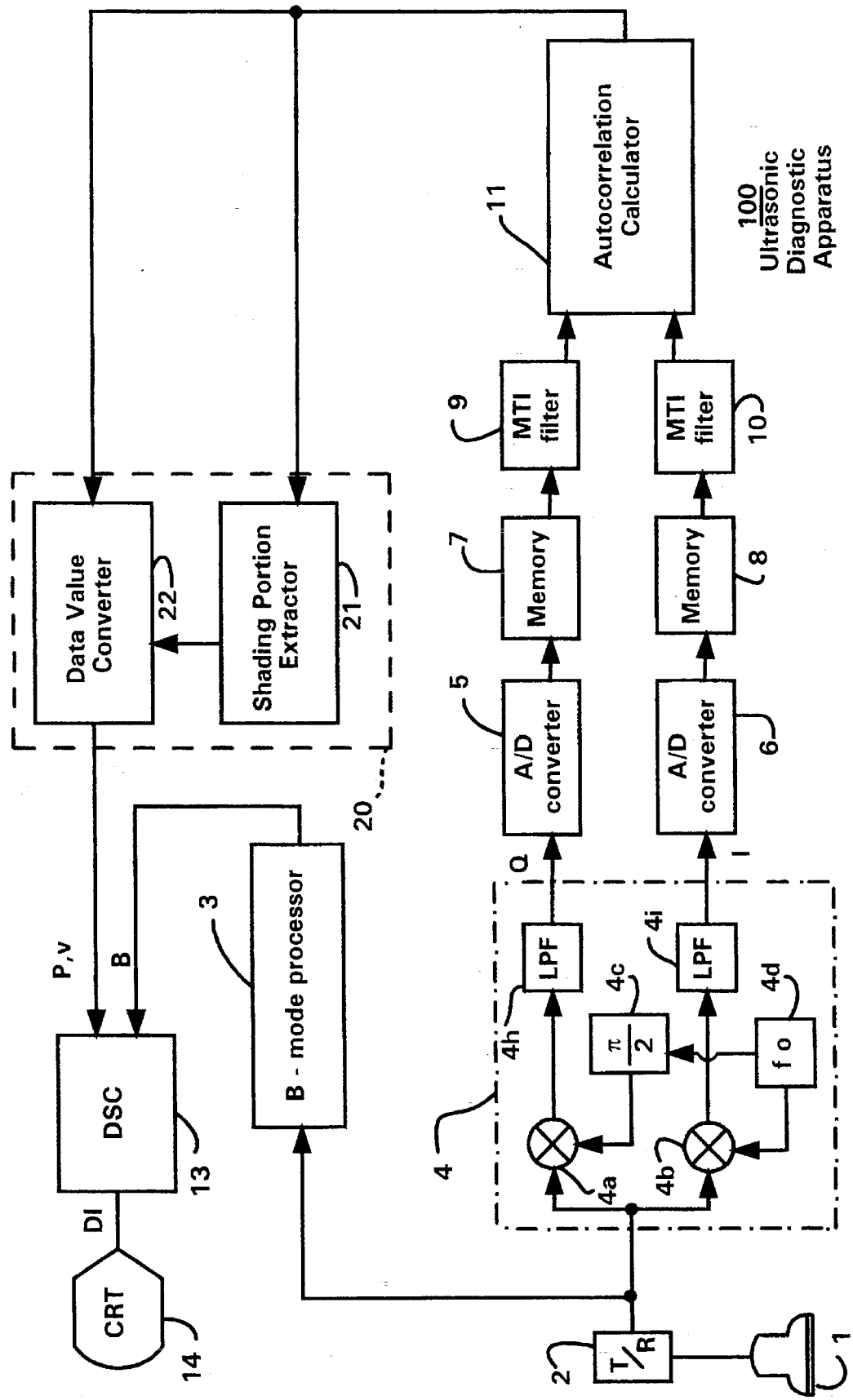
FIG. 1 is a block diagram showing the ultrasonic diagnostic apparatus based on a first embodiment of this invention.

In FIG. 1 showing a ultrasonic diagnostic apparatus 100 based on the first embodiment, a ultrasonic probe 1 and transmitter/receiver 2 operate in unison to transmit ultrasonic pulses at a certain time interval and receive ultrasonic echo signals from multiple observation points in depth direction on multiple ultrasonic beam lines.

In Doppler power mode, the ultrasonic echo signals are fed to an orthogonal detector 4. The orthogonal detector 4 includes mixers 4a and 4b, by which the ultrasonic echo signals are multiplied to reference signals provided by reference signal generators 4c and 4d, and it produces an orthogonal component Q and in-phase component I at the outputs of LPFs 4h and 4i. A/D converters 5 and 6 render the A/D conversion for the orthogonal component Q and in-phase component I, and store the resulting data in memories 7 and 8.

MTI filters 9 and 10 read the orthogonal component Q and in-phase component I out of the memories 7 and 8, and remove unneedful clutter components from these components Q and I. An autocorrelation calculator 11 calculates power data $P(R,\phi)$ (where R represents the depth of observation point and $\phi$ is the beam line number) from the orthogonal component Q and in-phase component I that have been rid of the unneedful components.

A shading portion extractor 21 extracts an image portion to be shaded from the power data $P(R,\phi)$ and delivers the result to a data value converter 22. The data value converter 22 converts the data value of the shading portion into the data value for shading and converts the data values of remaining portions into a value different from the data value for shading.

The shading portion extractor 21 and data value converter 22 are assumed to be formed of a microprocessor 20 which processes data as will be explained on the flowchart of FIG. 2, although these circuits 21 and 22 are actually formed of a buffer memory 201 and lookup table 202 as will be explained in connection with FIG. 6.

A DSC 13 converts the power data $P(R,\phi)$ into pixel values and implements the two-dimensional mapping for the pixel values based on the positions of observation points, thereby yielding image data DI. A CRT display unit 14 displays a ultrasonic image of Doppler power mode derived from the image data DI. For ultrasonic images of Doppler power mode, the background H is generally black, and blood vessels P1 and P2 are displayed in the orange color and at various luminance levels depending on the magnitude of the power.

In CFM mode, the autocorrelation calculator 11 implements the calculation of autocorrelation between ultrasonic pulses for the orthogonal component Q and in-phase component I, thereby producing velocity data $v(R,\phi)$. A DSC 13 converts the velocity data $v(R,\phi)$ into pixel values and implements the two-dimensional mapping for the pixel values based on the positions of observation points, thereby yielding image data DI.

The CRT display unit 14 displays a ultrasonic image of CFM mode derived from the image data DI. For ultrasonic images of CFM mode, the background is generally a B-mode image, and blood vessels are displayed in red and blue and at various luminance levels depending on the blood flow velocity and direction.

In B mode, the ultrasonic echo signals are fed to a B-mode processor 3. The B-mode processor 3 produces B-mode data from the magnitude of the ultrasonic echo signals and delivers the data to the DSC 13. The DSC 13 converts the B-mode data into pixel values and implements the two-dimensional mapping for the pixel values based on the positions of observation points, thereby yielding image data DI. The CRT display unit 14 displays a ultrasonic image of B mode derived from the image data DI. For ultrasonic images of B mode, the background is generally black, and tissues are displayed in achromatic colors of various luminance levels depending on the magnitude of the ultrasonic echo signals.

Figure 2:
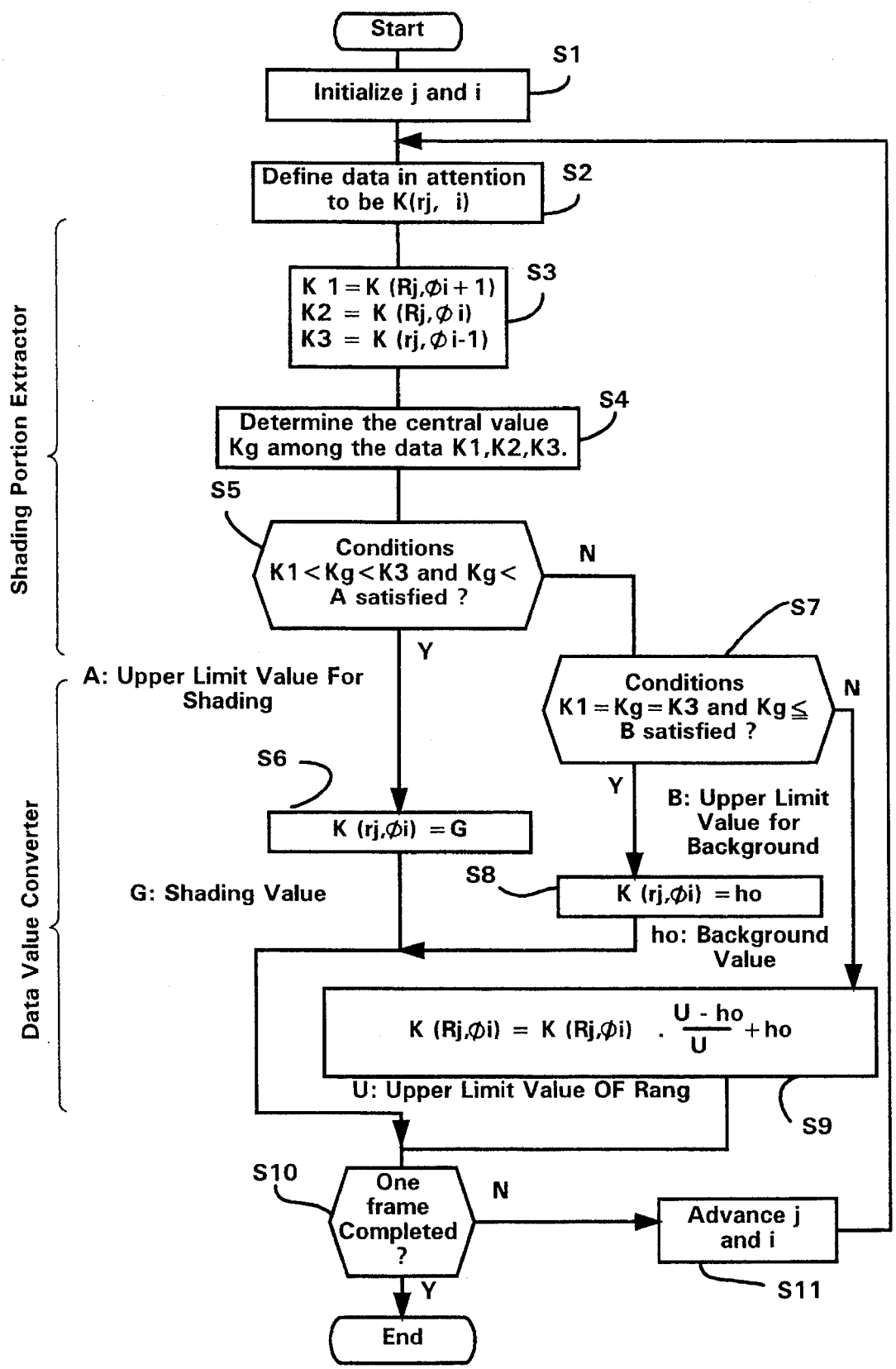
FIG. 2 is a flowchart of the shading portion extracting process and data value converting process.

FIG. 2 is a flowchart of the processing carried out by the microprocessor 20 having the functions of the shading portion extractor 21 and data value converter 22.

Step 1 initializes the observation point depth counter j and beam line number counter i.

Step 2 defines data in attention to be $k(R_j,\phi_i)$. This data is either power data $P(R,\phi)$ or velocity data $v(R,\phi)$.

Figure 3:
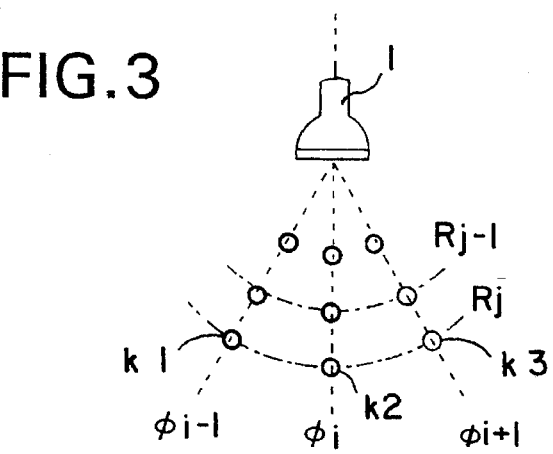
FIG. 3 is a diagram used to explain the positional relation among the observation points of data k1, k2 and k3.

Step 3 establishes data k1, k2 and k3 at three points on three contiguous beam lines with the same depth. FIG. 3 shows the positional relation of these three observation points of the data k1, k2 and k3.

Step 4 determines the central value kg among the data values k1, k2 and k3. The value kg is used later to eliminate the influence of noise. Instead of selecting the central value, the mean value of k1, k2 and k3 may be calculated.

Step 5 tests whether or not conditions k1<kg<k3 and kg≦A (where A is the upper limit value for shading) are satisfied. In case the condition k1<kg<k3 is met indicative of increases of data values in the ascending order of the beam line number, the portion of the data in the ultrasonic image is presumed to be the left-side profile section. With the upper limit value, which data of profile section can take, to be "A", the portion of the data is not the profile section unless the condition kg≦A is met even if the condition k1<kg<k3 is met. Accordingly, if an image portion satisfies the conditions k1<kg<k3 and kg≦A, it is very highly possible that the image portion is the left-side profile section. Based on these satisfied conditions, the image portion is extracted as a portion to be shaded, and the sequence proceeds to step 6. Otherwise, if at least one of the conditions k1<kg<k3 and kg≦A is not met, the sequence proceeds to step 7 without extracting the image portion. The steps 3,4 and 5 correspond to the shading portion extractor 21.

Figure 5A:
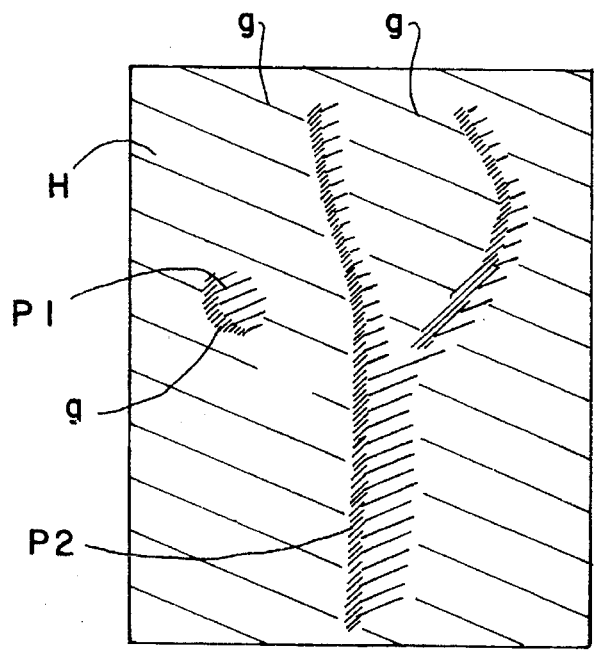
FIG. 5 is a diagram showing an example of ultrasonic images in Doppler power mode based on this invention.

Step 6 sets the data $k(R_j,\phi_i)$ in attention to be data value "G" for shading, and a shaded section g shown in FIG. 5 is produced. The sequence proceeds to step 10.

Step 7 tests whether or not conditions k1=kg=k3 and kg≦B (where B is the upper limit value for the background) are satisfied. In case the condition k1=kg=k3 is met indicative of equal data, the portion of the data is determined to be the section inside of the profile or the background. With the upper limit value which data of background can take to be "B", if condition kg≦B is met, the portion of the data is presumed to be the background. Accordingly, if an image portion satisfies the conditions k1=kg=k3 and kg≦B, it is very highly possible that the image portion is the background. Based on these satisfied conditions, the image portion is extracted as the background section, and the sequence proceeds to step 8. Otherwise, if at least one of conditions k1=kg=k3 and kg≦B is not met, the portion of the data is extracted as the section inside of the profile, and the sequence proceeds to step 9.

Step 8 sets the data $k(R_j,\phi_i)$ in attention to be data value "ho" (ho>G) for the background, and the background section H shown in FIG. 5 is produced. The sequence proceeds to step 10 thereafter.

Figure 4A:
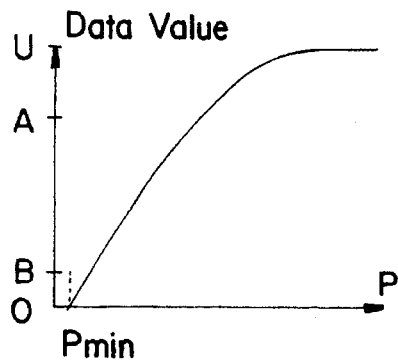
FIGS. 4A and 4B are diagrams used to explain data value conversion.
Figure 4A:
Figure 4B:
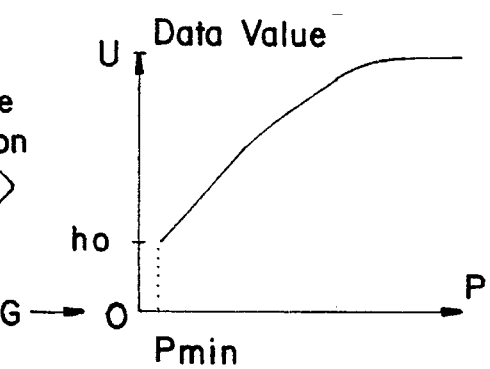

Step 9 compresses the value of the data $k(R_j,\phi_i)$ in attention to be within the range from ho to the upper limit value U of the range. FIGS. 4A and 4B show the concept of data value compression. Shown in FIG. 4A is the original range, which is compressed to the range shown in FIG. 4B having data values different (brighter) from the shading portion. The steps 7,8 and 9 correspond to the data value converter 22.

Steps 10 and 11 take place to repeat the operations of the step 2 through step 9 for one entire frame (e.g., j=1 to 60; i=1 to 1000). On completion of operations for the entire frame, the microprocessor 20 terminates the process.

FIG. 5 shows an example of ultrasonic images in Doppler power mode displayed by the ultrasonic diagnostic apparatus 100. The blood vessels P1 and P2 are displayed over the moderately bright background H, with dark shading g being added to the left side of the blood vessels P1 and P2. The blood vessels P1 and P2 appear as three-dimensional images, and the viewer can identify small blood vessels accurately.

Figure 6:
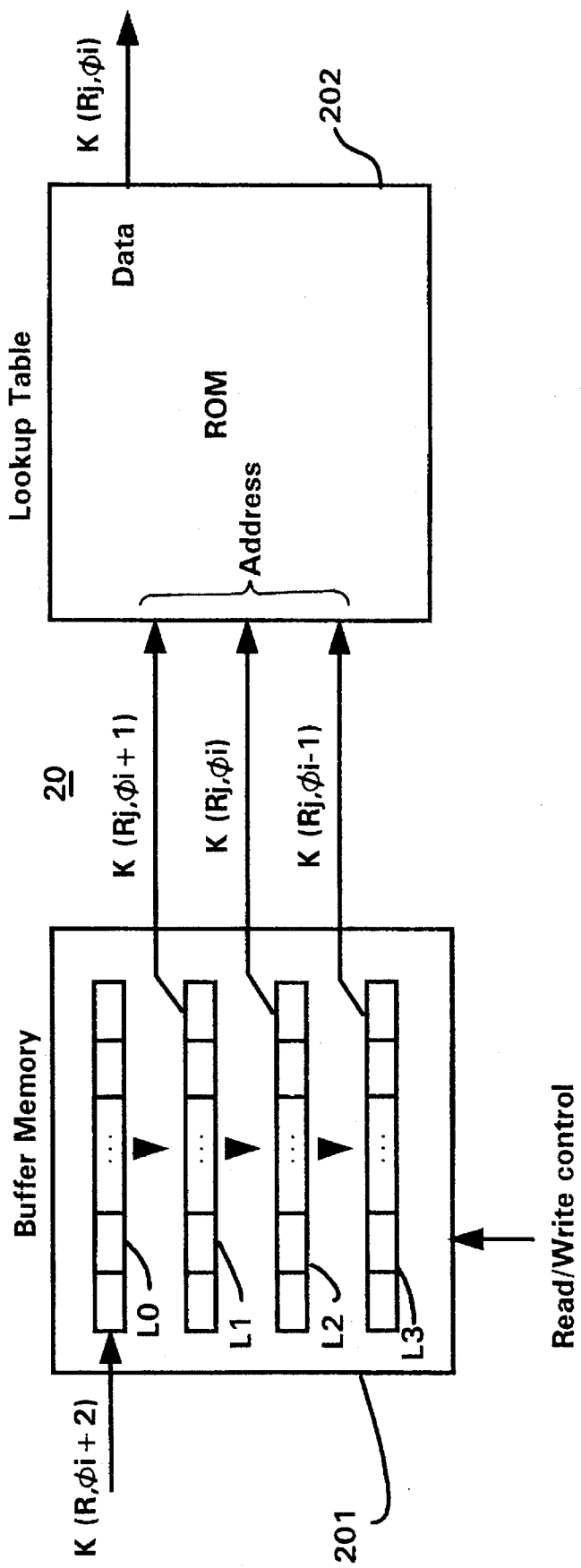
FIG. 6 is a block diagram showing the shading portion extractor and data value converter that are formed of a buffer memory and lookup table.

FIG. 6 is a block diagram showing the shading portion extractor 21 and data value converter 22 that are formed of a buffer memory 201 and lookup table 202. The buffer memory 201 consists of a shift register L0 in which a series of data of observation points on a ultrasonic beam line are shift-loaded sequentially and the data are read out in parallel, a shift register L1 which releases old contents in parallel and receives the output data from the shift register L0, a shift register L2 which releases old contents in parallel and receives the output data from the shift register L1, and a shift register L3 which releases old contents in parallel and receives the output data from the shift register L2.

Accordingly, the shift registers L1, L2 and L3 hold data $k(R,\phi i+1)$, $k(R,\phi i)$ and $k(R,\phi i-1)$ of adjoining beam lines, and these shift registers deliver data $k(Rj,\phi i+1)$, $k(Rj,\phi i)$ and $k(Rj,\phi i-1)$ of observation points of the same depth cyclically in the order of depth, i.e., in the ascending order of j. The data read/write operations of the shift registers L0, L1, L2 and L3 are controlled in synchronism with the reception of ultrasonic echo signals and the display of ultrasonic image.

The lookup table 202 is a ROM (Read Only Memory) for example, and it is addressed by the data $k(Rj,\phi i+1)$, $k(Rj,\phi i)$ and $k(Rj,\phi i-1)$ to release data $k(Rj,\phi i)$ which has been rendered the data value conversion. Accordingly, the process explained on the flowchart of FIG. 2 is carried out based on the referencing of the table. It requires shorter processing time and enables real-time processing.

The ultrasonic diagnostic apparatus 100 of the first embodiment operates to shade ultrasonic images of Doppler power mode or CFM mode on the left side of the profile so that blood vessels and other vessels such as the biliary duct are visualized as three-dimensional images, whereby the viewer can identify even small blood vessels accurately.

Embodiment 2

Figure 7:
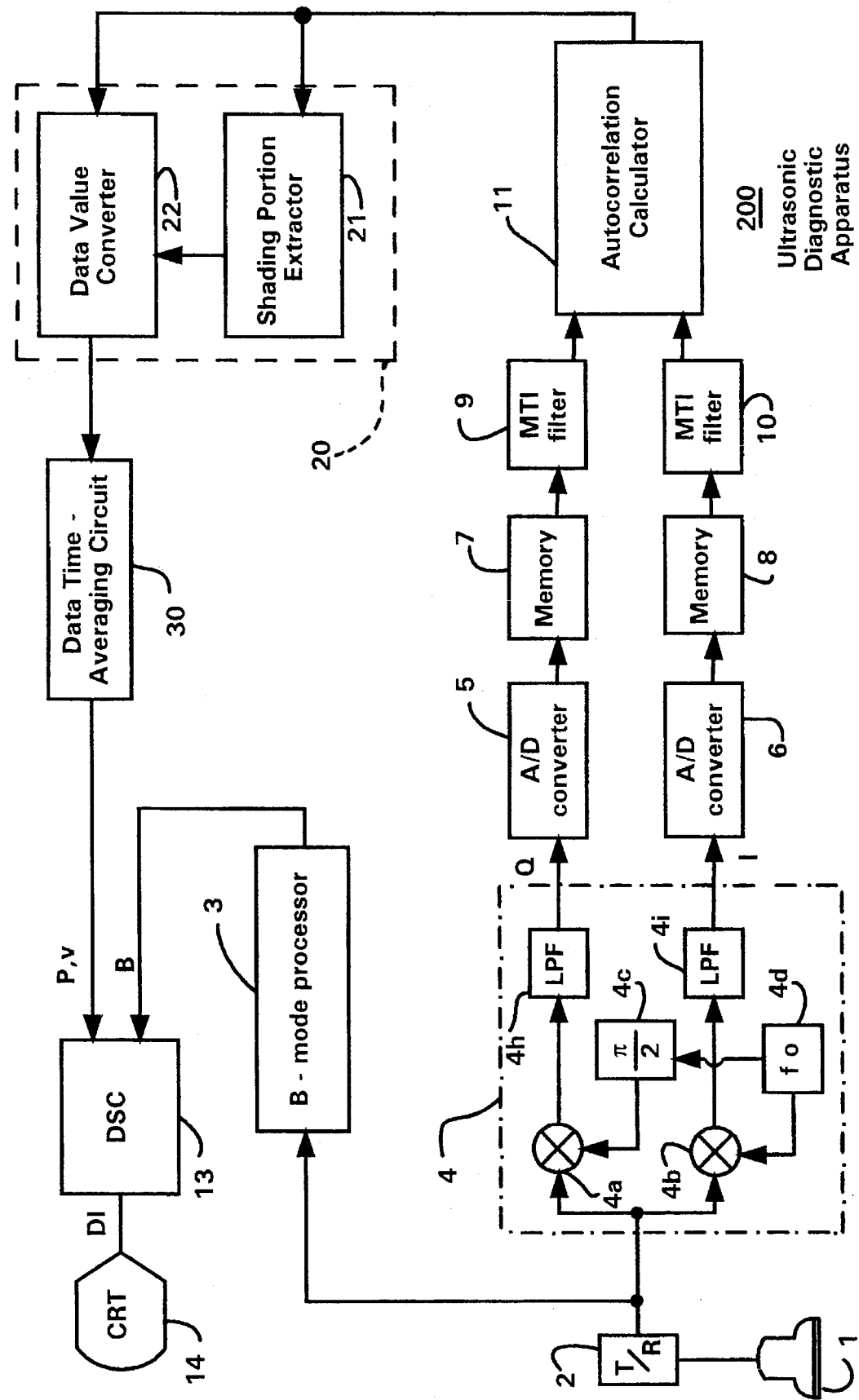
FIG. 7 is a block diagram showing the ultrasonic diagnostic apparatus based on a second embodiment of this invention.
Figure 8:
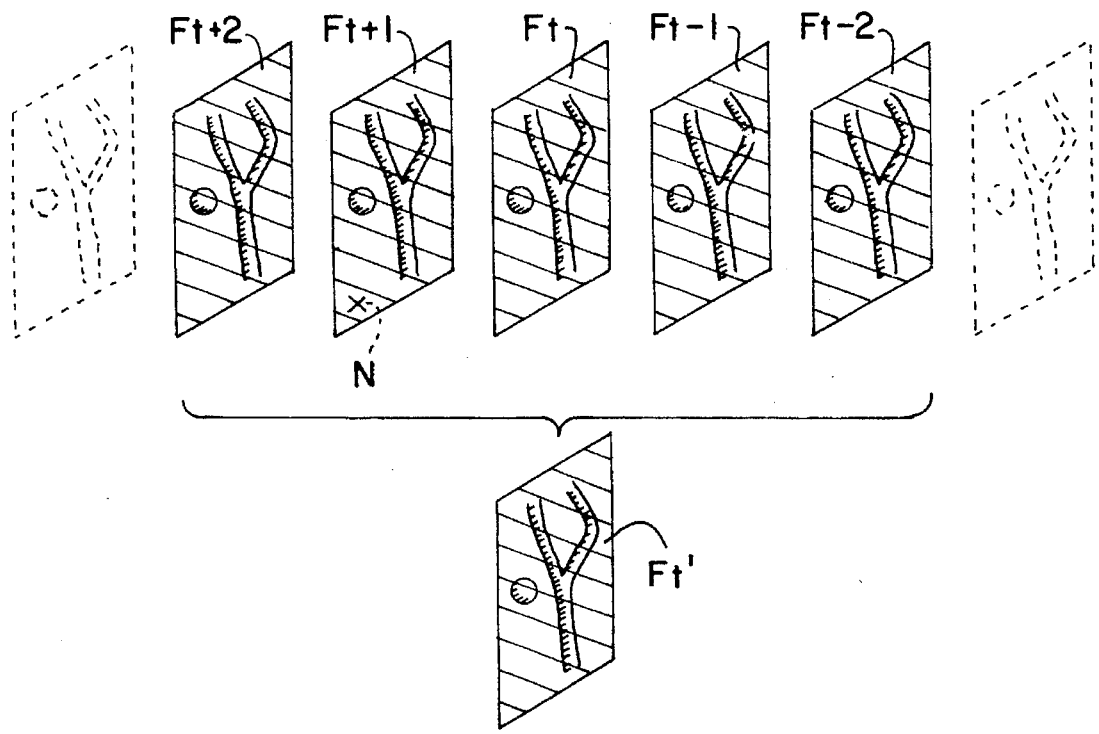
FIG. 8 is a diagram used to explain the movement-averaging for multiple frames.
Figure 10:
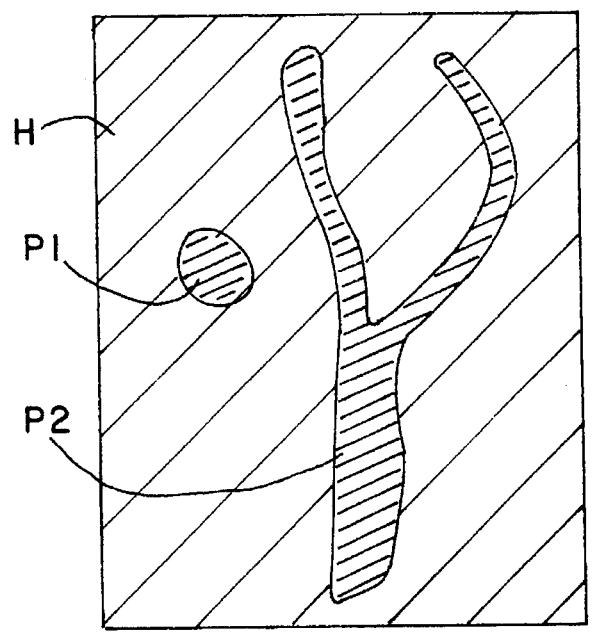
FIG. 10 is a diagram showing an example of ultrasonic images based on the conventional apparatus.
Figure 9:
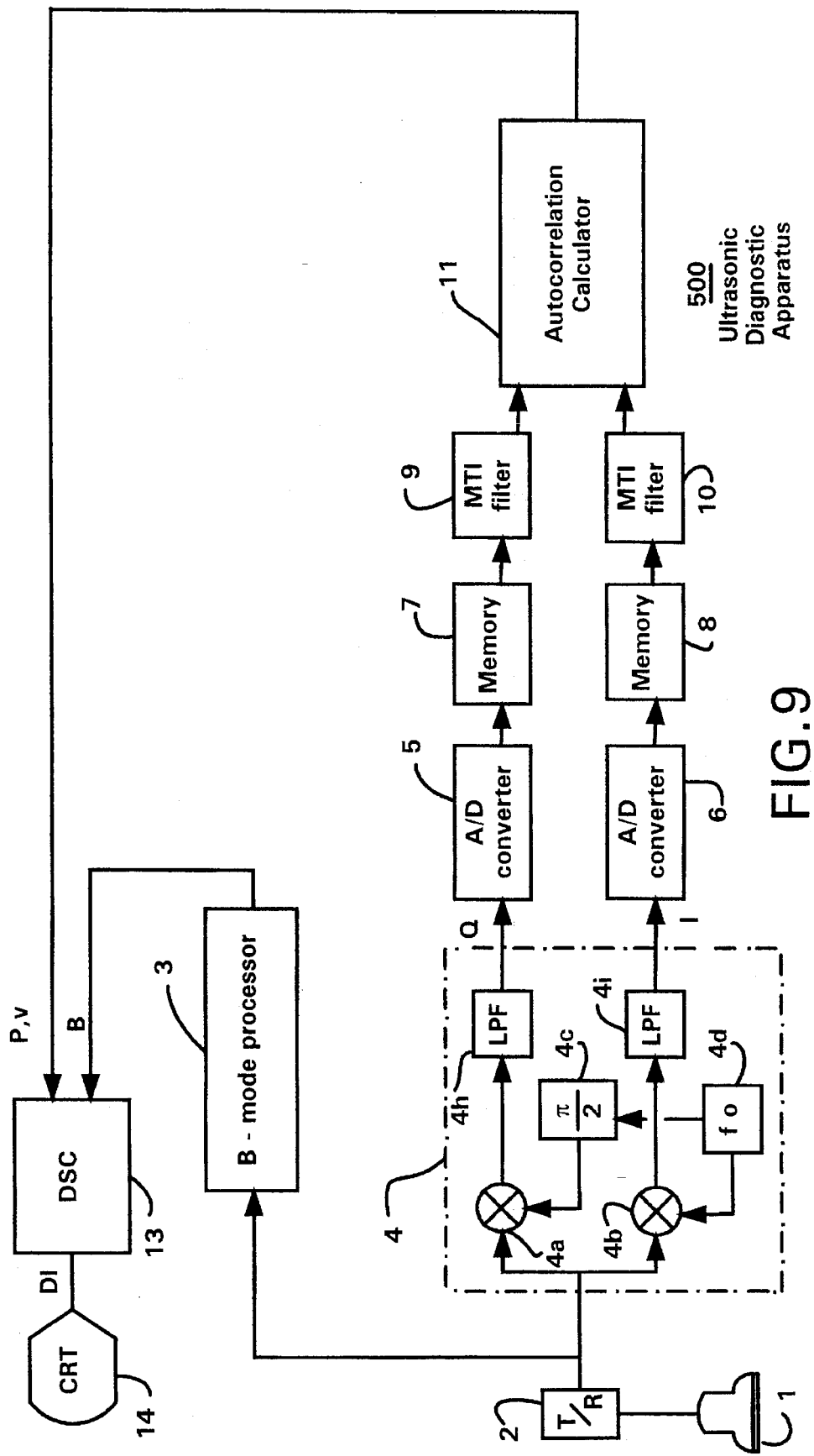
FIG. 9 is a block diagram of the conventional ultrasonic diagnostic apparatus.

FIG. 7 shows the arrangement of a ultrasonic diagnostic apparatus 200 based on the second embodiment of this invention. The ultrasonic diagnostic apparatus 200 has the same basic arrangement and operation as of the ultrasonic diagnostic apparatus 100 of the first embodiment (shown in FIG. 1), but it differs from the first embodiment in the addition of a data time-averaging circuit 30 connected between the combination of the shading portion extractor 50 and data value converter 20 and the DSC 13.

The data time-averaging circuit 30 calculates the movement-average value of data of multiple (five in this embodiment) consecutive frames Ft−2, Ft−1, Ft, Ft+1 and Ft+2 following the rendition of data value conversion, and delivers the resulting average value as data of a new frame Ft' to the DSC 13.

The ultrasonic diagnostic apparatus 200 of the second embodiment operates to shade the ultrasonic image of Doppler power mode or CFM mode on the left side of the profile so that vessels are visualized as three-dimensional images, whereby the viewer can identify even small blood vessels accurately. Moreover, in displaying ultrasonic images on a real-time basis, the continuous variation of the power of blood vessels is visualized as after images, and the viewer can identify blood vessels more accurately.

Variant embodiments (1) Instead of shading the image on the left side of the profile, the image may be shaded at the position below the profile by using data $k(Rj+1,\phi i)$, $k(Rj,\phi i)$ and $k(Rj-1,\phi i)$, or on the right side of the profile by replacing the condition k1<kg<k3 with k1>kg>k3 in step 5 on the flowchart of FIG. 2.

(2) Instead of using data $k(Rj,\phi i+1)$, $k(Rj,\phi i)$ and $k(Rj,\phi i-1)$ of three points, data of two points or data of four or more points may be used for the extraction of profile of image.

(3) The profile of image may be detected based on the calculation of differentiation.

(4) The data time-averaging circuit 30 may be connected between the autocorrelation calculator 11 and the combination of the shading portion extractor and data value converter 20.

(5) Instead of using data $P(R,\phi)$ and $v(R,\phi)$, image data $DI(x,y)$ may be used for the extraction of a shading portion and the data value conversion, although the amount of data to be processed will increase for the interpolation.

According to the method of displaying ultrasonic images and apparatus for ultrasonic diagnosis based on this invention, a ultrasonic image has its profile section partially shaded so that it is visualized as a three-dimensional image so as to facilitate the diagnosis. Particularly, in ultrasonic images of Doppler power mode, blood vessels are visualized as three-dimensional images, and the viewer can identify even small blood vessels accurately.

What is claimed is:

1. A method of displaying an ultrasonic image which transmits ultrasonic waves into a body under test, receives ultrasonic echo signals from inside of the body and displays an ultrasonic image produced from the ultrasonic echo signals, wherein said method comprises the step of shading part of a profile section of the image, and wherein ultrasonic images are shaded, and the shaded images are time-wise averaged, and the resulting averaged image is displayed, or ultrasonic images which are not shaded are time-wise averaged and the resulting averaged image is shaded and displayed.

2. The method of claim 1, where a range of pixel values of image portions that are not shaded does not include pixel values of the shaded portion.

3. An apparatus for ultrasonic diagnosis comprising data acquisition means which transmits ultrasonic waves and receives ultrasonic echo signals thereby to obtain data of observation points, image forming means which forms an ultrasonic image based on the data, and image display means which displays the image, wherein the image forming means shades a profile section of the image, and wherein further comprising data time averaging means which time-wise averages data released by a data value conversion means and delivers the averaged data to said image forming means, or data time averaging means which time-wise averages data obtained by said data acquisition means and delivers the averaged dat to a shading portion extraction means and said data value conversion means.

4. The apparatus of claim 3, wherein said shading portion extraction means and said data value convertion means comprise a buffer memory which holds ultrasonic beam line data and a lookup table which is addressed by beam line data held in said buffer memory.

5. The apparatus of claim 4, wherein said data comprises data of a Doppler power mode.

6. The apparatus of claim 3, wherein said data comprises data of a Doppler power mode.

7. An apparatus for ultrasonic diagnosis comprising data acquisition means which transmits ultrasonic waves along multiple ultrasonic beam lines in different directions and receives ultrasonic echo signals thereby to obtain data of multiple observation points on the beam lines, image forming means which forms an ultrasonic image based on the data, image display means which displays the image, and shading portion extraction means which extracts an image portion to be shade out of the data, and data value conversion means which converts the data value of the shaded portion into data value for shading and converts the data values of remaining portions into data value different from the data value for shading, and further comprising data time-averaging means for time-wise averaging data released by said data value conversion means and for delivering the averaged data to said image forming means, or data time-averaging means for time-wise averaging data obtained by said data acquisition means and for delivering the averaged data to said shading portion extraction means and said data value conversion means.

8. The apparatus of claim 7, wherein said shading portion extraction means and said data value conversion means comprise a buffer memory which holds ultrasonic beam line data and a lookup table which is addressed by the beam line data held in said buffer memory.

9. The apparatus of claim 8, wherein said data comprises data of a Doppler power mode.

10. The apparatus of claim 7, wherein said data comprises data of a Doppler power mode.

11. In a method of displaying an ultrasonic image, comprising the steps of transmitting ultrasonic waves into a body being tested;

receiving ultrasonic echo signals from inside of said body; and displaying an ultrasonic image produced from resulting ultrasonic echo signals;

the improvement comprising the step of adding a shaded part to a profile section of the ultrasonic image so that said profile section has the appearance of a three dimensional image.

12. The method of claim 11, wherein a range of pixel values of said profile section to which shading is not added does not include pixel values of the profile section to which shading is added.

13. An apparatus for ultrasonic diagnosis comprising:

data acquisition means for transmitting ultrasonic waves and for receiving ultrasonic echo signals thereby to obtain data of observation points;

image forming means for forming an ultrasonic image based on said data; and image display means for displaying said resulting image, wherein said image forming means comprises means for adding a shaded part to a profile section of said resulting image so that said profile section has the appearance of a three dimensional image.

14. The apparatus of claim 13 wherein image forming means comprises shading portion extraction means and data value conversion means, and wherein said shading portion extraction means and said data value conversion means comprise a buffer memory for holding ultrasonic beam line data and a lookup table which is addressed by said ultrasonic beam line data held in said buffer memory.

15. The apparatus of claim 13, wherein said data comprises data of Doppler power mode.

16. The apparatus of claim 13, wherein said image forming means comprises shading portion extraction means for extracting an image portion to which a shaded part is to be added, and data value conversion means for converting data value for shading and for converting data values of remaining portion into data value different from the data value fo shading.

17. The apparatus of claim 16, wherein said shading portion extraction means and said data value conversion means comprise a buffer memory which holds ultrasonic beam line data and a look up table which is addressed by the beam line data held in said buffer memory.

18. The apparatus of claim 16, wherein said data comprises data of Doppler power mode.

* * * * *